(12) United States Patent
John et al.

(10) Patent No.: US 8,655,041 B2
(45) Date of Patent: Feb. 18, 2014

(54) AUTOMATIC DETECTION OF CONTRAST INJECTION

(75) Inventors: Matthias John, Nürnberg (DE); Rui Liao, Princeton Junction, NJ (US); Michelle xiaohong Yan, Princeton, NJ (US); Wei You, Vancouver (CA)

(73) Assignee: Siemens Aktiengesellschaft, Munich (DE)

( * ) Notice: Subject to any disclaimer, the term of this patent is extended or adjusted under 35 U.S.C. 154(b) by 312 days.

(21) Appl. No.: 13/211,716

(22) Filed: Aug. 17, 2011

(65) Prior Publication Data

US 2012/0128226 A1 May 24, 2012

Related U.S. Application Data

(60) Provisional application No. 61/385,594, filed on Sep. 23, 2010.

(51) Int. Cl.
*G06K 9/00* (2006.01)
(52) U.S. Cl.
USPC ............................. 382/132; 382/130; 382/131
(58) Field of Classification Search
USPC .................................................. 382/130–133
See application file for complete search history.

(56) References Cited

U.S. PATENT DOCUMENTS

| | | | | |
|---|---|---|---|---|
| 6,368,285 | B1 * | 4/2002 | Osadchy et al. | 600/508 |
| 2005/0107688 | A1 * | 5/2005 | Strommer | 600/424 |
| 2010/0061611 | A1 * | 3/2010 | Xu et al. | 382/131 |
| 2012/0177277 | A1 * | 7/2012 | Florent et al. | 382/132 |
| 2013/0039559 | A1 * | 2/2013 | Grass et al. | 382/131 |

* cited by examiner

*Primary Examiner* — Vu Le
*Assistant Examiner* — Kenny Case
(74) *Attorney, Agent, or Firm* — Donald B. Paschburg; F. Chau & Associates, LLC (57) ABSTRACT

A method for automatically detecting the presence of contrast in an x-ray image includes acquiring an x-ray image prior to administration of contrast. A background image is estimated based on the x-ray image. The contrast is administered. A set of x-ray images is acquired. The background image is subtracted from the set of images. Image intensity is determined for each of the subtracted images. The subtracted images having highest image intensity are selected. A predefined shape model is fitted to the selected subtracted images. The fitting of the predefined shape model is used to fit the shape model to each of the subtracted images. A feature value is calculated for each image frame based on pixel intensities of each pixel fitted to the shape model for the corresponding subtracted image. An image frame of peak contrast is determined by selecting the image frame with the greatest feature value.

22 Claims, 3 Drawing Sheets

AUTOMATIC DETECTION OF CONTRAST INJECTION

CROSS-REFERENCE TO RELATED APPLICATION

The present application is based on provisional application Ser. No. 61/385,594, filed Sep. 23, 2010, the entire contents of which are herein incorporated by reference.

BACKGROUND

1. Technical Field

The present disclosure relates to detection of contrast and, more specifically, to the automatic detection of contrast injection.

2. Discussion of Related Art

Aortic valve diseases include aortic stenosis in which the aortic valve fails to fully open and aortic insufficiency in which the aortic valve does not properly prevent the backflow of blood. Both ailments may be life-threatening. Aortic valve disease may be treated by replacing the aortic valve. Traditionally, aortic valve replacement is performed during open heart surgery.

New minimally invasive approaches to aortic valve replacement have been developed. Such approaches may be referred to as percutaneous aortic valve replacement (PAVR) and may include trans-catheter aortic valve implantation (TAVI). Examples of TAVI include trans-apical TAVI in which antegrade access is used where the catheter and the prosthesis are inserted via small incisions in the chest and the apex of the left ventricle, and trans-femoral TAVI in which the catheter is inserted retrogradely via the femoral artery and the aortic arch.

Both trans-apical TAVI and trans-femoral TAVI use X-ray angiographic and fluoroscopic imaging to guide the procedure.

SUMMARY

A method for automatically detecting the presence of a contrast agent in an x-ray image includes acquiring a preliminary x-ray image of a region of interest of a subject prior to administration of the contrast agent. A background image is estimated based on the acquired preliminary x-ray image. The contrast agent is administered into the subject. A main set of x-ray images including a plurality of image frames is acquired. The estimated background image is subtracted from each image frame of the acquired main set of x-ray images to create a plurality of subtracted images corresponding to the plurality of image frames. A measure of image intensity is determined for each of the subtracted images. One or more of the subtracted images having a highest image intensity are selected. A predefined shape model is fitted to the selected one or more subtracted images. The fitting of the predefined shape model is used to fit the shape model to each of the plurality of subtracted images. A feature value is calculated for each image frame based on pixel intensities of each pixel fitted to the shape model for the corresponding subtracted image. An image frame of peak contrast is determined by selecting the image frame with the greatest feature value.

The estimation of the background may be updated as the main set of x-ray images are acquired based on one or more most recent image frames that are classified as not including contrast.

The measure of image intensity for each subtracted image may include generating a non-linear histogram mapping of each subtracted image. Selecting one or more of the subtracted images having a highest image intensity may include determining one or more highest histogram values.

Selecting the one or more subtracted images having a highest image intensity may include selecting a single subtracted image having the highest image intensity of the plurality of subtracted image and fitting the predefined shape model to the selected one or more subtracted images may include fitting the predefined shape model to the single subtracted image having the highest image intensity.

Selecting the one or more subtracted images having a highest image intensity may include selecting from two to five subtracted images having the highest image intensities of the plurality of subtracted images and fitting the predefined shape model to the selected one or more subtracted images may include calculating an average image based on the selected two to five subtracted images and fitting the predefined shape model to the calculated average image. Three subtracted images having the highest image intensities may be selected and calculating the average image may be performed using the three subtracted images having the highest image intensities.

Determining the measure of the image intensity for each of the subtracted images may be limited to a bound region defined within each subtracted image.

The predefined shape model may be modified in accordance with an anatomical structure of the subject prior to fitting.

Selecting the image frame with the greatest feature value may include generating a curve for feature value verses image frame number, smoothing the generated curve with a low-pass filter, identifying one or more local peaks within the smoothed curve, and selecting one of the identified local peaks as the image frame with the greatest feature value. One of the identified local peaks may be selected as the greatest feature value when the following criteria are met: the value of the local peak exceeds a predetermined value threshold, the local peak exhibits a pick-up gradient that exceeds a predetermined pick-up gradient threshold, and there are no other local peaks within a predetermined number of frames having a larger value.

The predefined shape model may represent an aortic root.

The method may additionally include applying a first template to each image frame to determine an extent to which the image frame resembles a potential contrast frame, applying a second template to each image frame to determine an extent to which the image frame resembles a non-contrast frame, and performing a likelihood ratio test to determine whether the image frame is more similar to the potential contrast frame or the non-contrast frame.

The method may additionally include selecting a set of contrast frames from among the plurality of image frames that have a feature value that is sufficiently close to the frame of peak contrast, selecting a set of non-contrast frames from among the plurality of image frames that have a feature value that is sufficiently far to the frame of peak contrast, training a local classifier using the selected set of contrast frames as positive training data and using the selected set of non-contrast frames as negative training data, and determining whether each of the frames of the plurality of image frames that are neither sufficiently close to the frame of peak contrast nor sufficiently far to the frame of peak contrast are contrast frames or non-contrast frames using the trained local classifier.

A method for registering a 2D fluoroscopic image of an aortic root to a 3D image of the aortic root includes acquiring a 3D image of the aortic root. A preliminary x-ray image of the aortic root is acquired of a subject prior to administration of a contrast agent. A background image is estimated based on the acquired preliminary x-ray image. The contrast agent is administered into the subject. A main set of x-ray images includes a plurality of image frames. The estimated background image is subtracted from each image frame of the acquired main set of x-ray images to create a plurality of subtracted images corresponding to the plurality of image frames. A measure of image intensity is determined for each of the subtracted images. One or more of the subtracted images having a highest image intensity are selected. A predefined shape model of the aortic root is fitted to the selected one or more subtracted images. The fitting of the predefined shape model to the one or more subtracted images is used to fit the shape model to each of the plurality of subtracted images. A feature value for each image frame is calculated based on pixel intensities of each pixel fitted to the shape model for the corresponding subtracted image. An image frame of peak contrast is determined by selecting the image frame with the greatest feature value. The 3D image of the aortic root is registered to the image frame determined to be of peak contrast.

Selecting the one or more subtracted images having a highest image intensity may include selecting from two to five subtracted images having the highest image intensities of the plurality of subtracted images and fitting the predefined shape model to the selected one or more subtracted images may include calculating an average image based on the selected two to five subtracted images and fitting the predefined shape model to the calculated average image. Three subtracted images having the highest image intensities may be selected and calculating the average image may be performed using the three subtracted images having the highest image intensities.

Selecting the image frame with the greatest feature value may include generating a curve for feature value verses image frame number, smoothing the generated curve with a low-pass filter, identifying one or more local peaks within the smoothed curve, and selecting one of the identified local peaks as the image frame with the greatest feature value. One of the identified local peaks may be selected as the greatest feature value when the following criteria are met: the value of the local peak exceeds a predetermined value threshold, the local peak exhibits a pick-up gradient that exceeds a predetermined pick-up gradient threshold, and there are no other local peaks within a predetermined number of frames having a larger value.

A computer system includes a processor and a non-transitory, tangible, program storage medium, readable by the computer system, embodying a program of instructions executable by the processor to perform method steps for automatically detecting the presence of a contrast agent in an x-ray image. The method includes acquiring a preliminary x-ray image of a region of interest of a subject prior to administration of the contrast agent. A background image is estimated based on the acquired preliminary x-ray image. The contrast agent is administered into the subject. A main set of x-ray images including a plurality of image frames are acquired. The estimated background image is subtracted from each image frame of the acquired main set of x-ray images to create a plurality of subtracted images corresponding to the plurality of image frames. A measure of image intensity is determined for each of the subtracted images. One or more of the subtracted images having a highest image intensity are selected. A predefined shape model is fitted to the selected one or more subtracted images. The fitting of the predefined shape model to the one or more subtracted images is performed to fit the shape model to each of the plurality of subtracted images. A feature value is calculated for each image frame based on pixel intensities of each pixel fitted to the shape model for the corresponding subtracted image and an image frame of peak contrast is determined by selecting the image frame with the greatest feature value.

The measure of image intensity for each subtracted image may include generating a non-linear histogram mapping of each subtracted image. Selecting one or more of the subtracted images having a highest image intensity may include determining one or more highest histogram values.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF TILE DRAWINGS

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention relate to the use of three-dimensional (3D) models to support TAVI procedures in which a 3D aortic model is overlaid onto fluoroscopy to provide anatomical details and more automatic and accurate C-ARM angulation for optimal valve deployment. The 3D model may be produced, for example, using a computed tomography (CT) scanner, a magnetic resonance (MR) image scanner, or by other suitable modalities.

Accurate overlay of 3D models onto fluoroscopy may utilize 2D/3D registration between the 3D model and the fluoroscopy. This registration may be achieved by matching the 3D model to the fluoroscopic image frames with contrast injection showing the aortic root. Identification of the frames of the fluoroscopy showing contrast may be performed manually; however, exemplary embodiments of the present invention provide approaches for automatically identifying contrast-enhanced fluoroscopic image frames so that optimal frames may be selected for use in registering the fluoroscopic image data to the 3D aortic model or for other purposes such as, for example, for performing motion compensation in image sequences.

Exemplary embodiments of the present invention provide for the automatic detection of contrast injection into the aortic root on fluoroscopy and/or angiography. The proposed method may be used to automatically trigger 2D/3D registration, to detect anatomical landmarks during TAVI procedures, and/or to compensate for motions such as patient movement, aortic root movement due to insertion of devices, and position change of the heart during rapid pacing. However, the disclosure should not be seen as limited to automatic detection of contrast injection solely for the purposes of TAVI procedures, and indeed automatic detection of contrast injection may be used for other purposes as well without departing from the disclosure.

Automatic detection of contrast injection, according to exemplary embodiments of the present invention, may provide for a more seamless workflow for motion compensation during TAVI, and this may accordingly increase the efficiency and efficacy of these relatively complicated hybrid-OR applications that may involve a large number of staff, equipment and steps.

In addition to detecting whether there is contrast injection in a fluoroscopy or angiography sequence, exemplary embodiments of the present invention may automatically detect a range of frames, of a sequence of frames, where the aortic root and/or ascending aorta are filled with contrast agent. The detected range of frames may then be used for 2D/3D registration and/or subsequent motion compensation.

Figure 1:
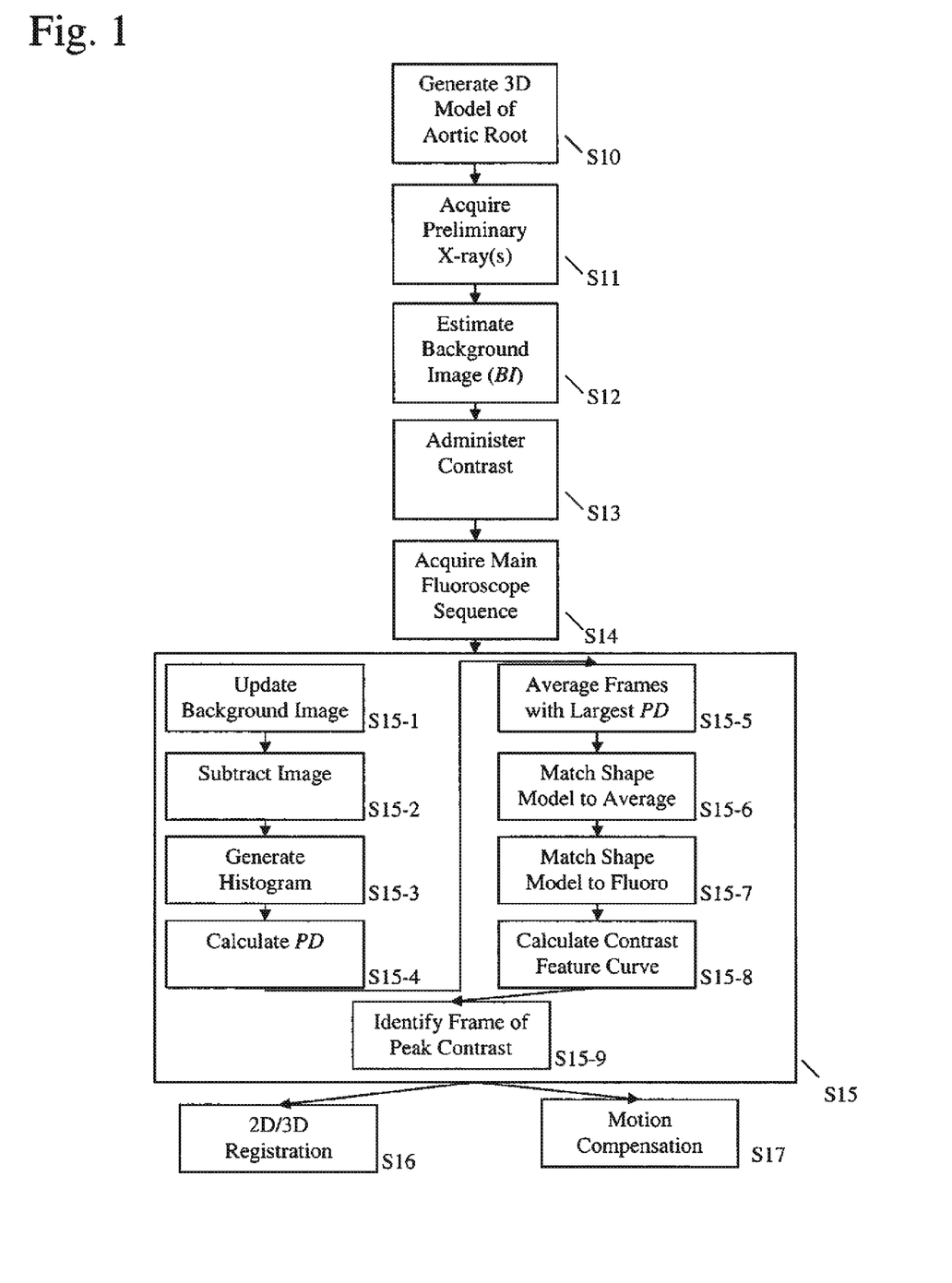
FIG. 1 is a flow chart illustrating a method for automatically detecting contrast in fluoroscopic image frames according to exemplary embodiments of the present invention.

FIG. 1 is a flow chart illustrating a method for automatically detecting contrast in fluoroscopic image frames according to exemplary embodiments of the present invention. First, a 3D model of the aortic root may be generated (Step S10). Generation of the 3D model may be performed, for example, by acquiring a 3D medical image such as an MRI or a CT scan. Alternatively, generation of the 3D model may be obtained with the use of an X-ray imager placed on a C-arm that captures imagery of the aortic root from at least two different angles so that the X-ray images may be combined to form the 3D model. This step may be performed where automatic detection of contrast is used for the purpose of 2D/3D registration, however, where automatic detection of contrast is for another purpose, the step of generating the 3D model may be omitted.

One or more preliminary X-ray image frames may be acquired (Step S11). The preliminary X-ray image frames may be acquired, for example, using a fluoroscope by capturing a limited number of frames. Acquisition of the preliminary X-ray image frame(s) may be performed prior to the administration of the radiocontrast agent so that image frame(s) that are known to exclude the contrast may be obtained. These pre-contrast image frame(s) may be used to produce an estimated background image (BI) (Step S12).

The radiocontrast agent may then be administered (Step S13). Administration may be performed either prior to the start of the acquisition of the main sequence (Step S14), or shortly thereafter. The radiocontrast agent, which may be referred to herein simply as contrast, may be a substance that is easily detectable from within an X-ray image such as those acquired by the fluoroscope. While any suitable contrast may be used, an iodinated agent is an example of a suitable contrast. The contrast may be administered intravenously A main sequence of fluoroscopic image frames may be acquired (Step S14). Automatic detection of the contrast agent may be performed based on the fluoroscopic image frames of the main sequence. The preliminary image frame(s) and the main sequence of image frames may, in practice, be acquired from a single set of fluoroscopic images. However, to minimize the radiation does that the patient is exposed to; image acquisition may be stopped after the preliminary image has been acquired and before the main sequence of image frames is acquired.

After the contrast has been administered (Step S13) and the main fluoroscopic image sequence commenced (Step S14), the monitoring of the image frames for the presence of the contrast may begin (Step S15).

According to an exemplary embodiment of the present invention, monitoring of the image frames for the arrival of the contrast may be limited to a particular region within the sequence of main fluoroscopic images. This region should include the aortic root and the immediately surrounding area. This region may be referred to herein as the region of aorta (ROA). The ROA may be defined as a rectangular region that encloses the aortic root. The ROA may be, for example, a size of 512×512 pixels for a 1024×1024 pixel image. Defining the ROA may be performed manually by a user or may be automatically derived, for example, from the C-arm CT volume position, when it is available.

Monitoring of the acquired fluoroscopic image frames for the presence of contrast, and in particular, monitoring the ROA thereof, may include several steps. For example, the background image BI may be updated (Step S15-1). As discussed above, initially, the background image may be assumed to be given at the beginning of a TAVI procedure, for example, by enforcing a short period of X-ray acquisition without contrast injection. Then, the background image may be updated online as the average of several most recent frames that are classified as non-contrasted. Online update of the background image may provide for a more robust detection of contrast with respect to dynamic changes in the background, e.g. due to table movement and/or insertion of devices.

Monitoring of the image frames may also include creating digitally subtracted images (Step S15-2). One digitally subtracted image may be created for each fluoroscopic image frame. The digitally subtracted images may show the difference between the acquired image frames and the background image, for example, as updated. Digitally subtracted images may be used to minimize the influence from the background in analyzing the imagery for the presence of contrast. The j-th digitally subtracted image $SI_j$ may be calculated as:

$$SI_j = BI - I_j \qquad (1)$$

where $I_j$ is the j-th frame of the main fluoroscope sequence and BI is the estimated background image.

The digitally subtracted images may be limited to the ROA, for example, as described above. The remainder of the image frames may be omitted from further analysis.

Next, a histogram may be generated for each digitally subtracted image (Step S15-3). The histogram may represent the distribution of pixel intensities within the subtracted image.

Due to automatic dose regulation in X-ray imaging systems, the background image obtained from previous sequences may have a different window width and/or level setting and hence a different intensity range from the current sequence to be processed. Histogram alignment between the background image and the current sequence may therefore be performed before the background image is used to calculate the digitally subtracted image for the current sequence. A nonlinear histogram mapping technique may be used for the alignment. For example, to align the intensity distribution of image $I_d$ to that of $I_f$ the grey value i in $I_d$ may be mapped to the grey value i' where $C_d(i) = C_f(i')$. Here $C_d(.)$ and $C_f(.)$ denote the cumulative density function (CDF) of $I_d$ and $I_f$ respectively.

For a discrete histogram distribution a perfect mapping typically might not be achieved and the following algorithm may be used to achieve an optimal approximation:

$$i \to i' = k : \min_{t_1 \le k \le t_2} |p_d(i) - p_f(k)| \quad (2)$$

where $t_1$ and $t_2$ defined by:

$$C_f(t_1-1) < C_d(i-1) \le C_f(t_1) \text{ and } C_f(t_2-1) < C_d(i) \le C_f(t_2) \quad (3)$$

Here $P_d(.)$ and $P_f(.)$ denote the histogram of $I_d$ and $I_f$ respectively. It may be assumed that there is no window width and/or level change during the acquisition of a given sequence, which is typically the case; hence the histogram of the background image may be mapped to that of an arbitrary frame of the current sequence. In order to minimize the influence from the contrast, if any, the histograms of the image excluding ROA may be mapped between the background image and an arbitrary frame.

Generation of the histograms may either be performed in real-time as each image is subtracted or after the entire main fluoroscopic image sequence has been acquired. In either event, each histogram may be analyzed to determine a measure of image intensity relative to the background (Step S15-4). This measure may be defined as a histogram-percentile-difference (PD). The PD may indicate the percent of the ROA pixels that are of a high intensity. A high PD may be indicative of an image with greater overall pixel intensity and may thereby suggest the presence of contrast.

For $SI_j$ (j=1 ... N), $PD_j$; may be calculated as the intensity difference between a threshold for a high PD (HH) (e.g. 75%) and a threshold for a low PD (HL) (e.g. 20%). The PD may be larger for frames with contrast and smaller for frames without contrast as long as the contrasted aorta occupies between 100-HH and 100-HL (e.g. between 25 and 80) percent of the whole ROA. This constraint may be viewed as relatively relaxed and accordingly, the underlined assumption may be safe considering the typical Field-of-View used during TAVI procedures.

The inter-frame motion of the aorta within a sequence may be negligible for contrast detection purpose. Accordingly, an average image $I_a$ may calculated from one or more, for example, three image frames with the largest PD (Step S15-5). This average image may be calculated by averaging the subtracted images corresponding to the image frames having the largest corresponding PDs. While this example is illustrated as using the top three image frames to form an average, alternatively, the image frame with the single highest PD may be used in place of the average image. Where an average image is calculated from multiple highest PD frames, the number of frames used is not limited to three. For example, two, four, five, six or more highest PD frames may be used.

A pre-defined aorta shape model SM may then be matched to the average image (Step S15-6), for example, using image-based 2D/2D registration. The 2D/2D registration may be performed once for the average image and the same registered model may be used for all the frames in the sequence. Five parameters $t=(t_x, t_y, \sigma, S_x, S_y)$ representing translation, rotation and scaling in 2D may be estimated by maximizing the difference between the average intensities within and outside the boundary of the aorta shape model and within the bounding box of SM:

$$\hat{t} = \max_t \left( \frac{1}{N_{in}} \sum_{p \in SM} I_a(p) - \frac{1}{N_{out}} \sum_{p \notin SM} I_a(p) \right) \quad (4)$$

The searching space for translation, rotation and scaling may be chosen to cover the possible variations observed across different patients/sequences/clinical sites.

The aorta shape model SM may be defined prior to the commencement of the procedure described herein. The shape model SM may include the aortic root and part of the ascending aorta, and may be calculated as the mean shape of several aortic shape models obtained by manual delineation of example aortic angiography from different patients/sequences. Since aorta is a tubular structure, its 2D projection onto the imaging plane is relatively invariant with respect to the rotation around the longitudinal axis, making 2D/2D registration in the imaging plane sufficient for rough detection of the aorta in the fluoroscopic/angiographic images.

The shape model SM need not be a fixed shape for all patients. For example, multiple shape models may exist and a most appropriate shape model may be selected for use with a given patient. Additionally, the alignment of SM may be optimized using other types of similarity measures, such as the gradient on the edge of the aorta. The SM may be optional during the whole procedure. Alternatively the ROA or the whole image could be used directly in histogram calculation. The SM may be used to make the contrast feature curve more peaky and hence to enhance the performance on contrast peak detection.

The matching of the shape model SM to the average image may then be used as a basis for matching the shape model SM to the full set of subtracted image frames (Step S15-7). Here, the shape model SM may be used as a binary mask that excludes the non-aorta pixels and maintains only the aorta pixels. These aorta pixels may be considered the image feature and the feature value may be defined as the sum of the intensities of the pixels of the feature.

Next, a contrast feature curve may be calculated (Step S15-8). The contrast feature curve is a representation of the feature values with respect to the frame number. Here, the histogram of $SI_j$ (j=1 ... N) for the area within the boundary of SM may be calculated for each frame and denoted by $HA_j$ (j=1 ... N). Two template histograms, $HA_{nc}$ and $HA_{pc}$, may be further calculated by averaging a few number of frames with the largest and smallest PD in the sequence respectively. For $SI_j$, the contrast feature $cf_j$ may be calculated as:

$$cf_j = S(HA_j, HA_{pc})/S(HA_j, HA_{nc}) \quad (5)$$

where $S(HA_1, HA_2)$ quantifies the similarity between two histograms $HA_1$ and $HA_2$ and is defined as:

$$S(HA_1, HA_2) = \sum_{l=1}^{bins} HA_1^l \times HA_2^l \quad (6)$$

Here $HA_i^l$ (i=1, 2) is the count in the l-th bin for histogram $HA_i$. It can be seen that the contrast feature cf is a ratio of two histogram similarities, suggesting that (a) it does not depend on the absolute value of the image intensity, making it relatively invariant with respect to variations in imaging physics and image formation; (b) it is normalized with respect to the size of the aorta, i.e. the total count of all bins for histogram $HA_j$; and (c) it is robust to the volume and density of the injected contrast because the similarity measure S in Eq. (6) is relatively invariant to the absolute distance between the peaks of the two histograms, as long as the two peaks are well-separated. The property of normalization of the contrast feature may make the classification of the contrasted frames relatively straightforward using a hard threshold.

When the sequence contains contrast injection, the two templates, $HA_{nc}$ and $HA_{pc}$, essentially represent the histograms of the aortic root with and without contrast injection respectively. In this case the contrast feature cf may essentially become a likelihood ratio test:

$$L(HA) = \frac{p(HA|H_1)}{p(HA|H_0)} \quad (7)$$

where $H_1$ and $H_0$ denote the contrasted and non-contrasted hypothesis respectively, and the conditional probability $P(HA|H_i)$ (i=0, 1) is assumed to be proportional to the similarity measure defined in Eq. (6). The likelihood ratio may be large for contrasted frames and small for non-contrasted frames. When the sequence does not contain any frames with contrast injection, $HA_{nc}$ and $HA_{pc}$ both represent the non-contrasted case, and the contrast feature then becomes close to 1 for all frames. For a given sequence, the minimum contrast feature $cf_{min}$ is further subtracted for all frames. The contrast feature curve therefore may be close to 0 for a sequence without contrast injection, and ranges from 0 to a large number (e.g., larger than 1.0) for a sequence with contrast injection.

The contrast feature curve may then be used to identify a frame of peak contrast (Step S15-9). Given a contrast feature curve, local peaks corresponding to one contrast injection may accordingly be detected. The contrast feature curve may first be smoothed by a low pass filter, and all local peaks may be detected from the smoothed curve. A local peak may be considered to correspond to one contrast injection where the following criteria are met: (a) its value is larger than a given threshold; (b) its pick-up gradient is larger than a given threshold; and (3) there is no other local peak within a certain number of frames that has a larger value. The pick-up gradient may be defined as the contrast feature value difference over a window of frames divided by the number of frames in the window.

Due to cardiac and respiratory motions, multiple local peaks may be detected for one contrast injection in the feature curve using the aforementioned criteria. In order to keep only one peak for one contrast injection, local peaks following a dominant peak within a certain number of frames may be removed. A dominant peak may be determined according to its large absolute contrast feature value and large pick-up gradient.

After the main fluoroscopic image frames have been successfully monitored for the presence of contrast (Step S15), this information may be used for the purpose of 2D-3D registration (Step S16) or motion compensation (Step S17). It may also be beneficial, either for the purposes of performing image registration, motion compensation, or for other purposes, to identify the range of frames with sufficient contrast injection at the aortic root and ascending aorta.

Figure 2:
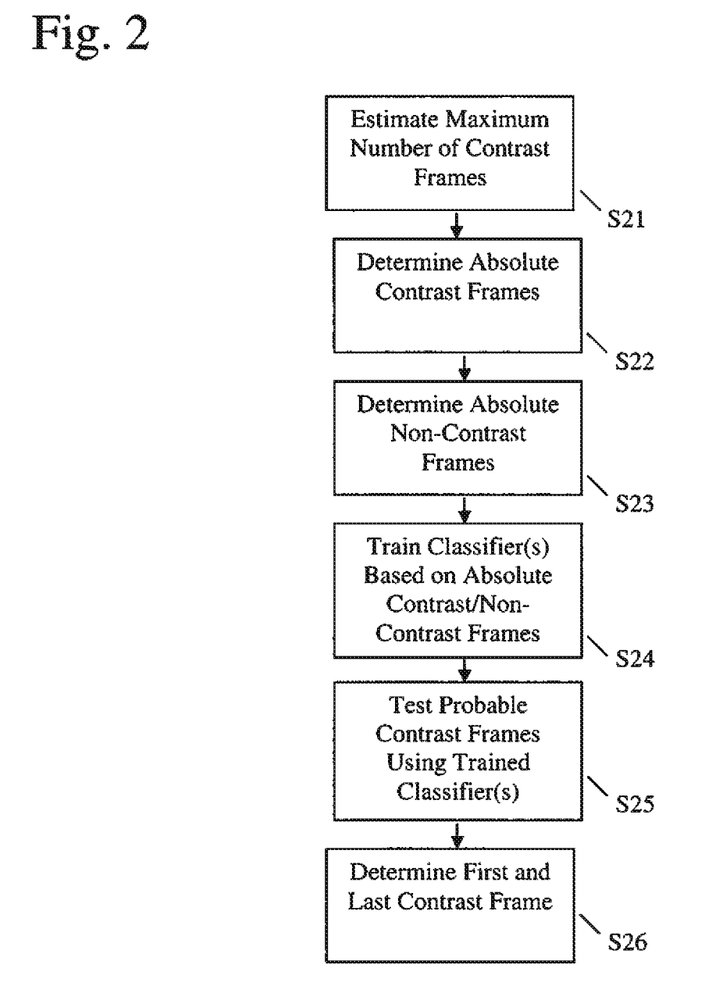
FIG. 2 is a flow chart illustrating a method for approximating a range of frames in which contrast fills the aortic root and ascending aorta that contain contrast given the detected peak of the contrast feature curve according to exemplary embodiments of the present invention.

FIG. 2 is a flow chart illustrating a method for approximating a range of frames in which contrast fills the aortic root and ascending aorta that contain contrast given the detected peak of the contrast feature curve according to exemplary embodiments of the present invention. First, the maximum possible number of contrasted frames may be estimated according to the frame rate and the typical contrast protocol for AVI procedures with respect to the maximal possible length of contrast injection in terms of seconds (Step S21).

Then, a range of absolute contrast frames is determined (Step S22). The absolute range may be a first-order approximation of the frames that contain contrast. The frames within the absolute range may in essence be those frames that are relatively close to the peak frame. The absolute range may be determined by propagating a frame counter from the detected peak frame Peak to the left (before the peak) and to the right (after the peak). The propagation may stops when: (a) the feature value falls below a given percentage of the peak value and is smaller than an absolute value, or (b) the maximum allowable number of frames on each side is reached. The maximum allowable number of frames on each side may be determined as a given percentage of the determined maximum possible length of contrast injection of step S21.

When a single threshold is used in identifying contrasted versus non-contrasted sequence, false positives or false negatives can occur. For example, a faint contrast with a lower feature value could result in a false negative, and an expanding balloon that resembles contrast injection could lead to a false positive. To deal with these cases, a double threshold may be used. The peaks above the high threshold are firstly confirmed as contrasted frames with high confidence, and the peaks below the low threshold are eliminated as non-contrasted. The lower amplitude peaks between the high threshold and the low threshold may be further classified by examining features such as the pickup gradient, or using a learning-based method. A classifier can be built off-line and the sequence with lower confidence from the contrast feature curve is further fed into this classifier for final confirmation.

Then, a set of non-contrasted frames may be identified. The non-contrasted frames may in essence be those frames that are relatively far from the peak frame. These frames may be found by continuing to propagate both left and right beyond the determined probable range until the feature value falls below a given percentage of the peak value or an absolute value (Step S23). It should be noted that the absolute value may be larger to the right of the probable range than to the left of the probable range as the contrast agent may tend to persist for a time after the peak.

One or more classifiers may then be trained using the contrasted and non-contrasted frames identified in the prior steps (Step S24). The contrasted frames may be used as positive training data and the non-contrasted frames may be used as negative training data.

Frames that are unidentified (neither being part of the probable contrast frames that are relatively close to the peak frame nor part of the non-contrasted frames that are relatively far from the peak frame) may then be tested using the locally trained classifier to get a binary class label representing whether a frame is contrasted or not (Step S25).

For contrast range detection, the outmost contrasted frames on each side of the detected peak are identified as the first frame when the majority of its neighboring frames within a certain window are labeled as non-contrasted by the trained classifier (Step S26).

Temporal may be modeled and then integrated into both the off-line and local classifier to identify whether a range of frames belong to a dynamic contrast injection process.

Moreover, 2D/3D Registration may be integrated into contrast detection to select those frames that are most suitable for registration purpose.

The proposed method is not limited to AVI applications, and can be straightforwardly extended for other type of interventions and/or hybrid-OR applications As discussed above, exemplary embodiments of the present invention may serve multiple purposes. For example, the methods described above may be used to automatically detect whether there is contrast injection for one or more frames in a fluoroscopic and/or angiographic sequence. These methods may be used to automate the workflow to register 3D volumes onto fluoroscopic scenes. These methods may be used to automate the location of anatomical features only visible under contrast injections. These methods may be used to identify and use the most recent non-contrasted frame as the background to account for dynamic brightness level or scene changes in the sequence. These methods may be used to learn the contrasted template frame and non-contrasted template frame on-line from the current sequence. These methods may be used to generate a feature curve representing the likelihood of having contrast injection, which is invariant to various imaging physics and formation. These methods may be used to utilize a generic aorta shape that is easy to obtain off-line. The shape constraint may allow for separated histograms for contrasted and non-contrasted frames. These methods may be used to not only detect one contrasted frame in one sequence, but also to detect a range of usable frames for 2D/3D registration and motion compensation. These methods may be used to utilize the image-based information in the current sequence, and may require minimum prior models or learning. These methods may fast, cost-effective, and may involve minimum user interaction.

Figure 3:
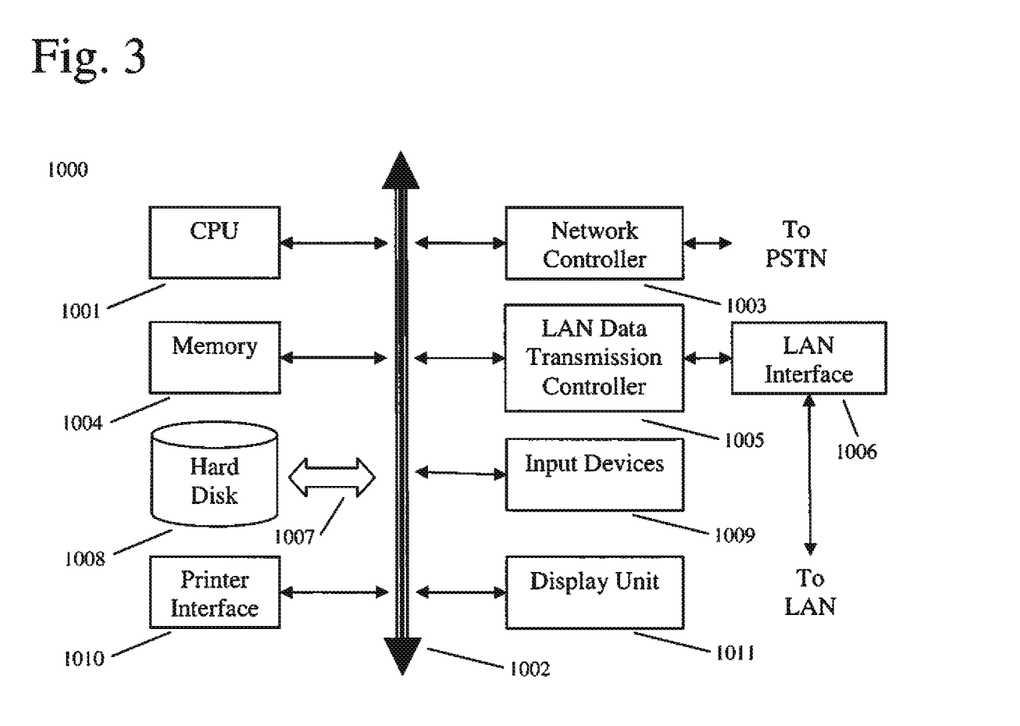
FIG. 3 shows an example of a computer system capable of implementing the method and apparatus according to embodiments of the present disclosure.

FIG. 3 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for automatically detecting the presence of a contrast agent in an x-ray image, comprising:
    acquiring a preliminary x-ray image of a region of interest of a subject prior to administration of the contrast agent;
    estimating a background image based on the acquired preliminary x-ray image;
    administering the contrast agent into the subject;
    acquiring a main set of x-ray images including a plurality of image frames;
    subtracting the estimated background image from each image frame of the acquired main set of x-ray images to create a plurality of subtracted images corresponding to the plurality of image frames;
    determining a measure of image intensity for each of the subtracted images;
    selecting one or more of the subtracted images having a highest image intensity;
    fitting a predefined shape model to the selected one or more subtracted images;
    using the fitting of the predefined shape model to the one or more subtracted images to fit the shape model to each of the plurality of subtracted images;
    calculating a feature value for each image frame based on pixel intensities of each pixel fitted to the shape model for the corresponding subtracted image; and
    determining an image frame of peak contrast by selecting the image frame with the greatest feature value.

2. The method of claim 1, wherein the estimation of the background is updated as the main set of x-ray images are acquired based on one or more most recent image frames that are classified as not including contrast.

3. The method of claim 1, wherein the measure of image intensity for each subtracted image includes generating a non-linear histogram mapping of each subtracted image.

4. The method of claim 3, wherein selecting one or more of the subtracted images having a highest image intensity includes determining one or more highest histogram values.

5. The method of claim 1, wherein selecting the one or more subtracted images having a highest image intensity includes selecting a single subtracted image having the highest image intensity of the plurality of subtracted image, and
    fitting the predefined shape model to the selected one or more subtracted images includes fitting the predefined shape model to the single subtracted image having the highest image intensity.

6. The method of claim 1, wherein selecting the one or more subtracted images having a highest image intensity includes selecting from two to five subtracted images having the highest image intensities of the plurality of subtracted images, and
    fitting the predefined shape model to the selected one or more subtracted images includes calculating an average image based on the selected two to five subtracted images and fitting the predefined shape model to the calculated average image.

7. The method of claim 6, wherein three subtracted images having the highest image intensities are selected and calculating the average image is performed using the three subtracted images having the highest image intensities.

8. The method of claim 1, wherein determining the measure of the image intensity for each of the subtracted images is limited to a bound region defined within each subtracted image.

9. The method of claim 1, wherein the predefined shape model is modified in accordance with an anatomical structure of the subject prior to fitting.

10. The method of claim 1, wherein selecting the image frame with the greatest feature value includes:
    generating a curve for feature value verses image frame number;
    smoothing the generated curve with a low-pass filter;
    identifying one or more local peaks within the smoothed curve; and
    selecting one of the identified local peaks as the image frame with the greatest feature value.

11. The method of claim 10, wherein one of the identified local peaks is selected as the greatest feature value when the following criteria are met:
    the value of the local peak exceeds a predetermined value threshold;
    the local peak exhibits a pick-up gradient that exceeds a predetermined pick-up gradient threshold; and
    there are no other local peaks within a predetermined number of frames having a larger value.

12. The method of claim 1, wherein the predefined shape model represents an aortic root.

13. The method of claim 1, additionally comprising:
applying a first template to each image frame to determine an extent to which the image frame resembles a potential contrast frame;
applying a second template to each image frame to determine an extent to which the image frame resembles a non-contrast frame; and
performing a likelihood ratio test to determine whether the image frame is more similar to the potential contrast frame or the non-contrast frame.

14. The method of claim 1, additionally comprising:
selecting a set of contrast frames from among the plurality of image frames that have a feature value that is sufficiently close to the frame of peak contrast;
selecting a set of non-contrast frames from among the plurality of image frames that have a feature value that is sufficiently far to the frame of peak contrast;
training a local classifier using the selected set of contrast frames as positive training data and using the selected set of non-contrast frames as negative training data; and
determining whether each of the frames of the plurality of image frames that are neither sufficiently close to the frame of peak contrast nor sufficiently far to the frame of peak contrast are contrast frames or non-contrast frames using the trained local classifier.

15. A method for registering a 2D fluoroscopic image of an aortic root to a 3D image of the aortic root, comprising:
acquiring a 3D image of the aortic root;
acquiring a preliminary x-ray image of the aortic root of a subject prior to administration of a contrast agent;
estimating a background image based on the acquired preliminary x-ray image;
administering the contrast agent into the subject;
acquiring a main set of x-ray images including a plurality of image frames;
subtracting the estimated background image from each image frame of the acquired main set of x-ray images to create a plurality of subtracted images corresponding to the plurality of image frames;
determining a measure of image intensity for each of the subtracted images;
selecting one or more of the subtracted images having a highest image intensity;
fitting a predefined shape model of the aortic root to the selected one or more subtracted images;
using the fitting of the predefined shape model to the one or more subtracted images to fit the shape model to each of the plurality of subtracted images;
calculating a feature value for each image frame based on pixel intensities of each pixel fitted to the shape model for the corresponding subtracted image;
determining an image frame of peak contrast by selecting the image frame with the greatest feature value; and
registering the 3D image of the aortic root to the image frame determined to be of peak contrast.

16. The method of claim 15, wherein selecting the one or more subtracted images having a highest image intensity includes selecting from two to five subtracted images having the highest image intensities of the plurality of subtracted images, and
fitting the predefined shape model to the selected one or more subtracted images includes calculating an average image based on the selected two to five subtracted images and fitting the predefined shape model to the calculated average image.

17. The method of claim 16, wherein three subtracted images having the highest image intensities are selected and calculating the average image is performed using the three subtracted images having the highest image intensities.

18. The method of claim 15, wherein selecting the image frame with the greatest feature value includes:
generating a curve for feature value verses image frame number;
smoothing the generated curve with a low-pass filter;
identifying one or more local peaks within the smoothed curve; and
selecting one of the identified local peaks as the image frame with the greatest feature value.

19. The method of claim 18, wherein one of the identified local peaks is selected as the greatest feature value when the following criteria are met:
the value of the local peak exceeds a predetermined value threshold;
the local peak exhibits a pick-up gradient that exceeds a predetermined pick-up gradient threshold; and
there are no other local peaks within a predetermined number of frames having a larger value.

20. A computer system comprising:
a processor; and
a non-transitory, tangible, program storage medium, readable by the computer system, embodying a program of instructions executable by the processor to perform method steps for automatically detecting the presence of a contrast agent in an x-ray image, the method comprising:
acquiring a preliminary x-ray image of a region of interest of a subject prior to administration of the contrast agent;
estimating a background image based on the acquired preliminary x-ray image;
administering the contrast agent into the subject;
acquiring a main set of x-ray images including a plurality of image frames;
subtracting the estimated background image from each image frame of the acquired main set of x-ray images to create a plurality of subtracted images corresponding to the plurality of image frames;
determining a measure of image intensity for each of the subtracted images;
selecting one or more of the subtracted images having a highest image intensity;
fitting a predefined shape model to the selected one or more subtracted images;
using the fitting of the predefined shape model to the one or more subtracted images to fit the shape model to each of the plurality of subtracted images;
calculating a feature value for each image frame based on pixel intensities of each pixel fitted to the shape model for the corresponding subtracted image; and
determining an image frame of peak contrast by selecting the image frame with the greatest feature value.

21. The computer system of claim 18, wherein the measure of image intensity for each subtracted image includes generating a non-linear histogram mapping of each subtracted image.

22. The computer system of claim 19, wherein selecting one or more of the subtracted images having a highest image intensity includes determining one or more highest histogram values.

* * * * *